United States Patent
Chou

(10) Patent No.: US 7,473,539 B2
(45) Date of Patent: Jan. 6, 2009

(54) METHODS FOR PRODUCING ALKYL ESTERS

(75) Inventor: Chih-Chung Chou, Yangmei Town (TW)

(73) Assignee: Sunho Biodiesel Corporation, Taipei (TW)

( * ) Notice: Subject to any disclaimer, the term of this patent is extended or adjusted under 35 U.S.C. 154(b) by 620 days.

(21) Appl. No.: 10/945,339

(22) Filed: Sep. 20, 2004

(65) Prior Publication Data

US 2006/0063241 A1    Mar. 23, 2006

(51) Int. Cl.
C12P 7/64 (2006.01)
C07C 51/43 (2006.01)

(52) U.S. Cl. ............................ 435/134; 554/174

(58) Field of Classification Search .............. 435/134; 554/174

See application file for complete search history.

(56) References Cited

U.S. PATENT DOCUMENTS

| | | | |
|---|---|---|---|
| 4,855,233 A | | 8/1989 | Gancet et al. |
| 5,288,619 A | * | 2/1994 | Brown et al. ............... 435/134 |
| 5,713,965 A | * | 2/1998 | Foglia et al. ............... 44/388 |
| 6,398,707 B1 | | 6/2002 | Wu et al. ................... 584/169 |
| 2003/0004363 A1 | | 1/2003 | Koncar et al. |

FOREIGN PATENT DOCUMENTS

| | | |
|---|---|---|
| CA | 2368179 | 9/2000 |
| DE | 101 22 551 A1 | 11/2002 |
| EP | 0 413 307 A1 | 2/1991 |
| EP | 1 111 064 A1 | 6/2001 |
| FR | 2 617 501 | 1/1989 |
| FR | 2616701 | 1/1989 |
| JP | 60-78587 | 5/1985 |
| JP | 62-104589 | 5/1987 |
| JP | 63-116697 | 5/1988 |

OTHER PUBLICATIONS

Soumanou et al., Improvement in Lipase-Catalyzed Synthesis of Fattey Acid Methyl Esters From Sunflower Oil, Enzyme and Microbial Technology 33 (2003), pp. 97-103.*

Abigor et al., "Lipase-catalyzed production of biodiesel fuel from some Nigerian lauric oil," Biochemical Society, 2000, 28:979-981.

Deng et al., "Enzymatic production of fatty acid alkyl esters with a lipase preparation from *Candida* sp. 99-125," Eur. J. Lipid Sci. Technol., 2003, 105:727-734.

Soumanou et al., "Lipase-catalyzed alcoholysis of vegetable oils," Eur. J. Lipid Sci. Technol., 2003, 105:656-660.

Dossat et al., "Continuous enzymatic Transesterification of High Oleic Sunflower Oil in a Packed Bed Reactor: Influence of the Glycerol Production", Enzyme and Microbial Technology 24;194-200, 1999.

Fukuda et al., "Biodiesel Fuel Production by Transesterification of Oils", Journal of Bioscience and Bioengineering, 92:405-416, 2001.

Mittelbach, "Lipase Catalyzed Alcoholysis of Sunflower Oil", Journal of American Oil Chemists' Society, 168-170, 1989.

Shimada et al., "Enzymatic Alcoholysis for Biodiesel Fuel Production and Application of the Reaction to Oil Processing", Journal of Molecular Catalysis B: Enzymatic 17:133-142, 2002.

Soumanou et al., "Improvement in Lipase-Catalyzed Synthesis of Fatty Acid Methyl Esters from Sunflower Oil", Enzyme and Microbial Technology, 33:97-103, 2003.

Viklund, "Surfactants based on Natural Products—Enzymatic Synthesis and Functional Characterization", Kungl Tekniska Hogskolan, Department of Biotechnology, Royal Institute of Technology, 11-17, 2003.

Chen, Doctoral Thesis, "Process Development for Transesterification of Triglyceride and Its Application," 77-85, 2003.

* cited by examiner

*Primary Examiner*—James O. Wilson
*Assistant Examiner*—Ebenezer Sackey
(74) *Attorney, Agent, or Firm*—Occhiuti Rohlicek & Tsao LLP

(57) ABSTRACT

This invention relates to a method for producing an alkyl ester via a transesterification or esterification reaction. The method includes (1) mixing an oil source containing a triglyceride or a carboxylic acid and a first primary alcohol or a first secondary alcohol in a first organic solvent to form a first solution; in which each molecule of the first organic solvent contains 4-8 carbon atoms and a heteroatom; (2) reacting the triglyceride or the carboxylic acid with the first primary alcohol or the first secondary alcohol in the presence of a first lipase to produce a first alkyl ester, in which the first solution does not undergo phase separation throughout the reaction; and (3) separating the first alkyl ester from the first solution.

40 Claims, No Drawings

METHODS FOR PRODUCING ALKYL ESTERS

BACKGROUND

Alcoholysis of vegetable oils and animal fats has been investigated extensively for producing fatty acid alkyl esters, which can be used as diesel fuels. Commonly used catalysts for alcoholysis include alkali hydroxides and alcoholates. These non-enzymatic catalysts are disadvantageous as they have to be removed with glycerol, a by-product, and cannot be reused. Further, purification of glycerol is difficult as it contains a large amount of such a catalyst.

As an alternative, lipases, enzymatic catalysts, have been used for preparing alkyl esters from natural oils in an enzymatic alcoholysis reaction. However, they may be inactivated by certain alcohols used or by glycerol produced from the alcoholysis reaction. Replacing or regenerating the lipases increases the costs. Thus, there exists a need to develop a cost-effective method of manufacturing alkyl esters on a commercially applicable scale, in which inactivation of lipases is minimized.

SUMMARY

This invention is based on the discovery that high purity alkyl esters can be readily produced from an oil feedstock (e.g., vegetable oils or animal fats) by a lipase-catalyzed reaction, in which inactivation of lipases is minimized.

In one aspect, this invention features a method for producing an alkyl ester via a transesterification or esterification reaction. The method includes (1) mixing an oil source containing a triglyceride or a carboxylic acid and a first primary alcohol or a first secondary alcohol in a first organic solvent to form a first solution; in which each molecule of the first organic solvent contains 4-8 carbon atoms and a heteroatom; (2) reacting the triglyceride or the carboxylic acid with the first primary alcohol or the first secondary alcohol in the presence of a first lipase to produce a first alkyl ester, in which the first solution does not undergo phase separation throughout the reaction; and (3) separating the first alkyl ester from the first solution.

Examples of a suitable oil source include plant oil (e.g., microalgae oil), animal oil (e.g., fish oil, lard, rendered fats, or tallow), waste grease (e.g., waste restaurant grease), or a hydrolytic fraction thereof (e.g., carboxylic acids). Before the mixing step, the oil source can be heated to 150-215° C. and cooled down to the reaction temperature.

Before the reaction, the oil source can be mixed with the first primary alcohol or the first secondary alcohol in the first organic solvent to form a one-phase solution. Examples of the first primary and secondary alcohols include those containing 1 to 18 carbon atoms, such as, methanol, ethanol, isopropanol, isobutanol, 3-methyl-1-butanol, hexanol, octanol, decanol, or lauryl alcohol. Examples of the first organic solvent include pyridine or a C4-C8 tertiary alcohol (e.g., t-butanol, 2-methyl-2-butanol, 2,3-dimethyl-2-butanol, 2-methyl-2-pentanol, 3-methyl-3-pentanol, 3-ethyl-3-pentanol, 2,3-dimethyl-2-pentanol, 2,3-dimethyl-3-pentanol, 2,2,3-trimethyl-3-pentanol, 2-methyl-2-hexanol, or 3-methyl-3-hexanol). The first organic solvent can also be mixed with other suitable solvents. Preferably, the first organic solvents can be mixed with an alkyl ester, which can be an alkyl ester obtained from the method of this invention or an alkyl ester obtained from other sources (e.g., purchased from a commercial source). When the first organic solvent is used together with another solvent, it is added in an amount sufficient to maintain the homogeneity of the first solution during the reaction, thereby minimizing the inactivation of the first lipase. The term "lipase" refers to any enzyme capable of catalyzing a transesterification or esterification reaction. Examples include candida antarctica lipase, thermomyces lanuginosa lipase, pseudomonas fluorescens lipase, pseudomonas cepacia lipase, or chromobacterium viscosum lipase. The first lipase can include a single lipase or a combination of two or more lipases. It is preferably immobilized on a carrier in the first reactor. The transesterification or esterification reaction can be carried out at 0-95° C. (e.g., 20-95° C.) for 1-180 minutes (e.g., 10-90 minutes or 20-60 minutes) to obtain the first alkyl ester.

During a transesterification reaction between an oil source containing a triglyceride and a first primary or secondary alcohol, glycerol is produced as a by-product. Unexpectedly, the first alkyl ester can be easily obtained by phase separation between the first alkyl ester and the glycerol after removing the first organic solvent and the unreacted first primary or secondary alcohol by evaporation. The just-mentioned oil source may also contain monoglycerides, diglycerides, or carboxylic acids. Monoglycerides and diglycerides react with the first primary or secondary alcohol in a manner similar to triglyceride. The carboxylic acids react with the first primary or secondary alcohol via an esterification reaction, in which water is produced as a by-product and can be readily removed during the evaporation process.

During an esterification reaction between an oil source containing a carboxylic acid and a first primary or secondary alcohol, water (but no glycerol) is produced as a by-product. It is also unexpected that the first alkyl ester can be easily obtained by removing the first organic solvent, the unreacted first primary or secondary alcohol, and the water by evaporation. When the just-mentioned oil source contains a significant amount of triglycerides, diglycerides, or monoglycerides, the first alkyl ester can be obtained in the manner described in the preceding paragraph.

If the first alkyl ester obtained above is contaminated with monoglycerides, diglycerides, triglyceride, or carboxylic acid, the contaminants can be removed by further reacting with an alcohol via another transesterification or esterification reaction. Specifically, the first alkyl ester can be mixed with a second primary alcohol or a second secondary alcohol in a second organic solvent to form a second solution. Each molecule of the second organic solvent contains 4-8 carbon atoms and a heteroatom. The second organic solvent can be the same or different from the first organic solvent. The second primary or secondary alcohol is preferably the same as the first primary or secondary alcohol. The monoglycerides, diglycerides, triglyceride, or carboxylic acid in the second solution can then react with the second primary alcohol or the second secondary alcohol in the presence of a second lipase to produce a second alkyl ester. In the reaction, the second solution does not undergo phase separation. The second lipase can be the same or different from the first lipase. The first and second alkyl esters thus obtained can then be separated from the second solution. Preferably, the second alkyl ester is identical to the first alkyl ester.

The details of one or more embodiments of the invention are set forth in the description below. Other features, objects, and advantages of the invention will be apparent from the description and from the claims.

DETAILED DESCRIPTION

This invention relates to a method of preparing alkyl esters from a feedstock via an enzymatic transesterification or esterification reaction. Below is an example of manufacturing alkyl esters:

First, an oil source containing a triglyceride (e.g., a soybean oil) is mixed with a first primary or secondary alcohol (e.g., anhydrous methanol) in a first organic solvent (e.g., an anhydrous C4-C8 tertiary alcohol or anhydrous pyridine) in a first mixer to form a first one-phase solution. The oil source can be degummed or refined. Preferably, it contains a minimum amount of phospholipids (e.g., less than 0.2 wt % or less than 0.001 wt %). Typically, the amount of first primary or secondary alcohol is about 10-50 mol % in excess of the stoichiometric amount required for the complete conversion of the oil source. The first organic solvent is inert in the subsequent lipase-catalyzed reaction (i.e., does not react with triglyceride to any significant level or inactivate the lipase). When the oil source contains fatty acids, pyridine can be used as the first organic solvent. Optionally, the first organic solvent can be mixed with another organic solvent, such as an alkyl ester. Use of an alkyl ester as a co-solvent prolongs the life span of a lipase for the subsequent transesterification or esterification reaction. The mixing step can be carried out at the reaction temperature or at any other suitable temperature.

Before the mixing step, the oil source can also be heated to 150° C. to 215° C. for a period of time (e.g., 5-60 minutes) and then cooled down to the reaction temperature. The heating time varies depending on the oil source used. Use of heat-treated oil sources unexpectedly shortens the reaction time.

Next, the first one-phase solution thus obtained is fed into a first reactor, which is filled with a first lipase immobilized on a carrier. The first reactor can be a packed bed reactor (e.g., a plug flow reactor), or any other suitable reactor known in the art. Typically, the first reactor is kept at a constant temperature (e.g., 0-95° C.) during the reaction. The first solution preferably contains less than 10,000 ppm (e.g., less than 5,000 ppm) by weight of water before it is sent to the first reactor. The flowing rate of the first solution through the reactor is so controlled that the residence time is about the same as the estimated reaction time. The reaction time, which can be determined empirically, depends on the lipase used or the composition of the first solution. Typically, it ranges from 1-180 minutes. During the reaction, the first solution is homogenous and does not undergo any phase separation, thereby minimizing inactivation of the first lipase by glycerol or the first primary or secondary alcohol.

The effluent from the first reactor is then fed into a first vacuum evaporator, which can be stripped with nitrogen or deaerated superheated steam. The vacuum evaporator can be a falling film evaporator, a thin film evaporator, a column evaporator, or any other suitable evaporator known in the art. The temperature and pressure in the first evaporator can vary depending on the first organic solvent and the first primary or secondary alcohol used in the preceding reaction. Typically, the temperature is lower than 120° C. and the pressure is lower than 100 mmHg. Water (either contained in the oil source or produced during the reaction), the first organic solvent, and the unreacted first primary or secondary alcohol are removed in the first evaporator. They can then be collected and separated (in a pure form or as a mixture) from each other in a recovery unit, which consists of a series of liquid separation or removal units. Water removed from the recovery unit is typically sent to a water-treatment facility and discarded.

The first organic solvent and the unreacted first primary or secondary alcohol can be recovered and re-used in the mixing step mentioned above. Preferably, they contain a minimum amount of water so that the first solution contains less than 10,000 ppm by weight of water before it is sent to the first reactor.

The residue leaving the first vacuum evaporator can then be cooled down and sent to a first liquid-liquid separator. The temperature of the separator can be maintained at 20-80° C. to minimize the formation of any solid. In the separator, the residue is allowed to sit to form two layers. Glycerol, a by-product, forms the bottom layer. It can be easily collected from the separator and further purified by removing the residual amount of water, the first organic solvent, and the unreacted first primary or secondary alcohol in a vacuum evaporator. The upper layer contains the first alkyl ester and can be used without further purification in certain applications, such as lubricant oils, emulsifiers, cleaning agents, and solvents. The first alkyl ester thus obtained can also be used as a co-solvent in the first solution. A liquid-liquid separator may not be required to purify an alkyl ester obtained from an esterification reaction between an oil source containing a carboxylic acid and an alcohol as no glycerol is produced as a by-product.

The first alkyl ester obtained above can further react with an alcohol via another transesterification or esterification reaction to remove contaminants. Specifically, the first alkyl ester can be sent to a second mixer and mixed with a second primary or secondary alcohol in a second organic solvent to form a second one-phase solution. Preferably, the second primary or secondary alcohol is the same as the first primary or secondary alcohol. The amount of the second primary or secondary alcohol and the second organic solvent is such that the second solution does not undergo any phase separation during the subsequent transesterification or esterification reaction. This amount can be in excess to expedite the completion of the subsequent reaction. It can be up to the same amount as that added in the first mixer.

The second solution is then sent to a second reactor, which contains a carrier immobilized with a second lipase. The second reactor is kept at a constant temperature and is typically the same as that of the first reactor. The residence time in the second reactor is generally less than that in the first reactor, and can be determined empirically. The effluent from the second reactor is then sent to a second vacuum evaporator, in which water, the second organic solvent, and the unreacted second primary or secondary alcohol are removed and sent to the recovery unit mentioned above. The residue from the second vacuum evaporator is then sent to a second liquid-liquid separator. The by-product glycerol is separated from the residue and combined with that obtained from the first liquid-liquid separator. A high purity alkyl ester can be obtained from the second liquid-liquid separator. It can be used as diesel fuels, lubricant oils, or chemical intermediates. It can also be used as a co-solvent in the first solution mentioned above.

The process described above can be carried out by a batch method or a flow method, i.e., a continuous manufacturing process. Typically, a flow method can be used to help maintain reasonable manufacturing costs. As a lipase generally loses activity after being exposed to an elevated temperature beyond a time limit, the flow process may be stopped or switched to another reactor system after operation for a certain period of time so as to prolong the life span of the lipase. The life span of a lipase varies depending on the reaction temperature, the type of the lipase, and the type of the organic solvent. The flow method may not need to be stopped or switched to another reactor system when the transesterification or esterification reaction is carried out at or below room temperature.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

EXAMPLE 1

Soybean oil was used as an oil source for preparing alkyl esters. Specifically, refined soybean oil (55.4 wt %) was mixed with anhydrous methanol (8.6 wt %), and anhydrous t-butanol (36.0 wt %) in a first mixer to form a one-phase solution. The solution was then sent to a first reactor, which was filled with NOVOZYM 435 (a candida antarctica lipase; Novozymes A/S, Bagsvaerd, Denmark). Specifically, NOVOZYM 435 was immobilized on a carrier (a macroporous resin) and was then placed in the reactor. The temperature of the reactor was 45° C. The reaction time was 62 minutes. After the reaction was completed, the solution was fed into a vacuum evaporator and then a liquid-liquid separator to obtain a product. The composition of the product was determined by HPLC (column: Luna Su C18(2) 250×4.6 mm, phenomenex; mobile phases: methanol, hexane, and isopropanol; UV detector: UV-2075, JASCO, Japan). Unexpectedly, the product obtained contained 96.19 wt % alkyl esters, 3.59 wt % monoglycerides and diglycerides, and 0.22 wt % triglycerides.

In another experiment, an alkyl ester was used as a co-solvent. Specifically, refined soybean oil (49.1 wt %) was mixed with anhydrous methanol (7.6 wt %), anhydrous t-butanol (20.5 wt %), and an alkyl ester (22.8 wt %) in a first mixer to form a one-phase solution. The reaction conditions were the same as those described above except that the reaction completed in 58.0 minutes. Unexpectedly, the product obtained contained 96.10 wt % alkyl esters, 3.23 wt % monoglycerides and diglycerides, and 0.67 wt % triglycerides.

In still another experiment, t-amyl alcohol and an alkyl ester were used as solvents. Specifically, refined soybean oil (40.8 wt %) was mixed with anhydrous methanol (6.3 wt %), anhydrous t-amyl alcohol (37.3 wt %), and an alkyl ester (15.6 wt %) in a first mixer to form a one-phase solution. The reaction conditions were the same as those described above except that the reaction completed in 53.0 minutes. Unexpectedly, the product obtained contained 96.96 wt % alkyl esters, 2.64 wt % monoglycerides and diglycerides, and 0.40 wt % triglycerides.

EXAMPLE 2

An alkyl ester obtained from Example 1 was mixed with anhydrous methanol and anhydrous t-butanol in another mixer to form a one-phase solution. The solution thus formed contained 70.00 wt % of the alkyl ester, 2.8 wt % of contaminants (i.e., 2.47 wt % of monoglycerides and diglycerides and 0.31 wt % of triglycerides), 7.28 wt % of the methanol, and 19.94 wt % of the t-butanol. The solution was then sent to another reactor, which was filled with NOVOZYM 435. Specifically, NOVOZYM 435 was immobilized on a carrier and then placed in the reactor. The temperature of the second reactor was 45° C. The reaction time was 17.5 minutes. After the reaction was completed, the solution was fed into another vacuum evaporator and then another liquid-liquid separator to obtain a product. The composition of the product was determined by HPLC.

Unexpectedly, the product obtained above contained 99.24 wt % alkyl esters, 0.65 wt % monoglycerides and diglycerides, and 0.11 wt % triglycerides.

EXAMPLE 3

Oil sources other than soybean oil were used as starting materials for preparing alkyl esters in a manner similar to that described in Example 1. Oil sources used included waste restaurant grease containing high free fatty acids, waste restaurant grease containing low free fatty acids, tallow, lard, fish oil, palm oil, and castor oil. In one experiment, waste restaurant grease containing high free fatty acids was used. Specifically, the reactor containing NOVOZYM 435 was fed with a solution containing such waste restaurant grease (49.1 wt %), anhydrous methanol (7.6 wt %), t-butanol (20.5 wt %), and an alkyl ester (22.8 wt %). Specifically, NOVOZYM 435 was immobilized on a carrier and then placed in the reactor. The temperature of the reactor was 45° C. The reaction time was 24.0 minutes. The product from the reactor was isolated and its composition was determined by HPLC. Unexpectedly, the product obtained above contained 96.63 wt % alkyl esters, 3.17 wt % monoglycerides and diglycerides, and 0.20 wt % triglycerides.

In another experiment, fish oil (an animal oil) was used as an oil source. Specifically, fish oil (52.4 wt %) was mixed with anhydrous methanol (7.8 wt %), and anhydrous pyridine (39.8 wt %) in a first mixer to form a one-phase solution. The reaction conditions were the same as those described above except that the reaction completed in 25.0 minutes. Unexpectedly, the product obtained contained 95.63 wt % alkyl esters, 3.03 wt % monoglycerides and diglycerides, and 1.34 wt % triglycerides.

In still another experiment, palm oil (a plant oil) was used as an oil source. Specifically, plant oil (46.5 wt %) was mixed with anhydrous methanol (7.5 wt %), and anhydrous t-amyl alcohol (46.0 wt %) in a first mixer to form a one-phase solution. The reaction conditions were the same as those described above except that the reaction completed in 41.0 minutes. Unexpectedly, the product obtained contained 96.97 wt % alkyl esters, 1.95 wt % monoglycerides and diglycerides, and 1.08 wt % triglycerides.

EXAMPLE 4

Primary alcohols were used as starting materials for preparing alkyl esters in a manner similar to that described in Example 1. Alcohols used included methanol, ethanol, isobutanol, 3-methyl-1-butanol, hexanol, octanol, decanol, and lauryl alcohol. In one experiment, the reactor containing NOVOZYM 435 was fed with a solution containing fish oil (52.0 wt %), ethanol (11.2 wt %), and anhydrous t-butanol (36.8 wt %). Specifically, NOVOZYM 435 was immobilized on a carrier and then placed in the reactor. The temperature of the reactor was 45° C. The reaction time was 39.0 minutes. The product from the reactor was isolated and its composition was determined by HPLC. Unexpectedly, the product obtained above contained 97.44 wt % alkyl esters, 1.44 wt % monoglycerides and diglycerides, and 1.11 wt % triglycerides.

In another experiment, hexanol (a C6 alcohol) was used as a starting material. Specifically, soybean oil (53.7 wt %) was mixed with anhydrous hexanol (26.6 wt %), and anhydrous t-butanol (19.7 wt %) in a first mixer to form a one-phase solution. The reaction conditions were the same as those described above except that the reaction completed in 46.0 minutes. Unexpectedly, the product obtained contained 95.06 wt % alkyl esters, 4.11 wt % monoglycerides and diglycerides, and 0.88 wt % triglycerides.

In still another experiment, lauryl alcohol (a C12 alcohol) was used as a starting material. Specifically, soybean oil (37.2 wt %) was mixed with anhydrous lauryl alcohol (33.6 wt %), and anhydrous t-butanol (29.2 wt %) in a first mixer to form a one-phase solution. The reaction conditions were the same as those described above except that the reaction completed in 66.0 minutes. Unexpectedly, the product obtained contained 95.03 wt % alkyl esters, 4.07 wt % monoglycerides and diglycerides, and 0.90 wt % triglycerides.

EXAMPLE 5

Secondary alcohols were used as starting materials for preparing alkyl esters in a manner similar to that described in Example 1. Alcohols used included isopropanol (a C3 alcohol), 2-butanol (a C4 alcohol), and secondary n-octyl alcohol (a C8 alcohol). In one experiment, the reactor containing NOVOZYM 435 was fed with a solution containing rapeseed oil (52.9 wt %), isopropanol (14.1 wt %), and anhydrous t-amyl alcohol (33.0 wt %). Specifically, NOVOZYM 435 was immobilized on a carrier and then placed into the reactor. The temperature of the reactor was 45° C. The reaction time was 39.0 minutes. The product from the reactor was isolated and its composition was determined by HPLC. Unexpectedly, the product obtained above contained 93.92 wt % alkyl esters, 4.86 wt % monoglycerides and diglycerides, and 1.22 wt % triglycerides.

In another experiment, 2-butanol was used as a starting material. Specifically, soybean oil (52.5 wt %) was mixed with anhydrous 2-butanol (18.9 wt %), and anhydrous t-amyl alcohol (28.6 wt %) in a first mixer to form a one-phase solution. The reaction conditions were the same as those described above except that the reaction completed in 46.0 minutes. Unexpectedly, the product obtained contained 92.84 wt % alkyl esters, 5.08 wt % monoglycerides and diglycerides, and 2.09 wt % triglycerides.

In still another experiment, secondary n-octyl alcohol was used as a starting material. Specifically, soybean oil (46.4 wt %) was mixed with anhydrous secondary n-octyl alcohol (29.3 wt %), and anhydrous t-butanol alcohol (24.3 wt %) in a first mixer to form a one-phase solution. The reaction conditions were the same as those described above except that the reaction completed in 42.0 minutes. Unexpectedly, the product obtained contained 94.69 wt % alkyl esters, 2.45 wt % monoglycerides and diglycerides, and 2.86 wt % triglycerides.

EXAMPLE 6

An alkyl ester was prepared using lauric acid and methanol as starting materials via an esterification reaction in a manner similar to that described in Example 1. Specifically, the reactor containing NOVOZYM 435 was fed with a solution containing anhydrous lauric acid (77.7 wt %), anhydrous methanol (17.6 wt %), and anhydrous t-butanol (4.7 wt %). NOVOZYM 435 was immobilized on a carrier and then into the reactor. The temperature of the reactor was 45° C. The reaction time was 37.0 minutes. The product from the reactor was isolated and its composition was determined by GC (8610C, SRI, USA; column: MXT-65TG, length: 30 m, I.D.: 0.25 μm; carrier gas: He, flow rate: 1 ml/min; injector: split ratio: 20 to 1, temperature: 300° C.; detector: FID, temperature: 370° C.).

Unexpectedly, the product obtained above contained 96.0 wt % methyl laurate and 4.0 wt % lauric acid.

EXAMPLE 7

Alkyl esters were prepared using soybean oil and methanol as starting materials in a manner similar to that described in Example 1 except that the soybean oil was heated for a period of time before use. Specifically, the soybean oil was first heated either at 200° C. for 5 minutes or at 210° C. for 1 hour and then cooled down to the reaction temperature. Subsequently, the soybean oil (49.1 wt %) was mixed with anhydrous methanol (7.6 wt %), anhydrous t-butanol (20.5 wt %), and an alkyl ester (22.8 wt %) in the mixer to form a one-phase solution. The solution was then sent to the reactor, which was filled with NOVOZYM 435. Specifically, NOVOZYM 435 was immobilized on a carrier and was placed into the reactor in advance. The temperature of the reactor was 45° C. Each product from the reactor was isolated and its composition was determined by HPLC.

Unexpectedly, it took 50.3 minutes and 47.4 minutes to obtain a product containing less than 1.5 wt % triglycerides using soybean oil heated at 200° C. for 5 minutes and using soybean oil heated at 210° C. for 1 hour, respectively. In comparison, it took 53.8 minutes to do so in a similar reaction condition using soybean oil without prior heat treatment.

EXAMPLE 8

LIPOZYME TL IM (a thermomyces lanuginosa lipase, Novozymes A/S, Bagsvaerd, Denmark) was used as a catalyst for preparing alkyl esters in a manner similar to that describe in Example 1. Specifically, it was immobilized on a granulated silica carrier and then placed in the reactor. The reactor was then fed with a solution containing soybean oil (49.1 wt %), anhydrous methanol (7.6 wt %), anhydrous t-butanol (20.5 wt %), and an alkyl ester (22.8 wt %). The temperature of the reactor was 45° C. The reaction time was 51.0 minutes. The product from the reactor was isolated and its composition was determined by HPLC.

Unexpectedly, the product obtained above contained 94.04 wt % alkyl esters, 3.65 wt % monoglycerides and diglycerides, and 2.31 wt % triglycerides.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A method for producing an alkyl ester, comprising:
   mixing an oil source containing a triglyceride and a first primary alcohol or a first secondary alcohol in a first organic solvent to form a first solution; wherein each molecule of the first organic solvent contains 4-8 carbon atoms and a heteroatom;
   reacting the triglyceride with the first primary alcohol or the first secondary alcohol in the presence of a first lipase to produce a first alkyl ester, wherein the first solution does not undergo phase separation throughout the reaction and glycerol is produced as a by-product; and obtaining the first alkyl ester by phase separation between the alkyl ester and the glycerol after removing the first organic solvent and the unreacted first primary or first secondary alcohol by evaporation.

2. The method of claim 1, wherein the first organic solvent is a C4-C8 tertiary alcohol.

3. The method of claim 2, wherein the first organic solvent is t-butanol, 2-methyl-2-butanol, 2,3-dimethyl-2-butanol, 2-methyl-2-pentanol, 3-methyl-3-pentanol, 3-ethyl-3-pentanol, 2,3-dimethyl-2-pentanol, 2,3-dimethyl-3- pentanol, 2,2,3-trimethyl-3-pentanol, 2-methyl-2-hexanol, or 3-methyl-3-hexanol.

4. The method of claim 1, wherein the first organic solvent is pyridine.

5. The method of claim 1, wherein the first primary alcohol or the first secondary alcohol contains 1 to 18 carbon atoms.

6. The method of claim 1, wherein the oil source is plant oil, animal oil, waste grease, or a hydrolytic fraction thereof.

7. The method of claim 1, wherein the first lipase is immobilized on a carrier.

8. The method of claim 7, wherein the first lipase is candida antarctica lipase, thermomyces lanuginosa lipase, pseudomonas fluorescens lipase, pseudomonas cepacia lipase, or chromobacterium viscosum lipase.

9. The method of claim 1, wherein the reacting step is carried out at 0-95°C.

10. The method of claim 1, wherein the reacting step is carried out in 1-180 minutes.

11. The method of claim 1, further comprising heating the oil source to 150-215° C. and cooling the heated oil source down to the reaction temperature before the mixing step.

12. The method of claim 1, further comprising adding an alkyl ester to the first solution before the reacting step.

13. The method of claim 1, further comprising:
mixing the first alkyl ester obtained from the separation step and a second primary alcohol or a second secondary alcohol in a second organic solvent to form a second solution, wherein the first alkyl ester is contaminated with monoglycerides, diglycerides, triglyceride, or carboxylic acid, and each molecule of the second organic solvent contains 4-8 carbon atoms and a heteroatom;

reacting the monoglycerides, diglycerides, triglyceride, or carboxylic acid with the second primary alcohol or the second secondary alcohol in the presence of a second lipase to produce a second alkyl ester, wherein the second solution does not undergo phase separation throughout the reaction; and separating both the first and second alkyl esters from the second solution.

14. The method of claim 13, wherein the first organic solvent or the second organic solvent is a C4-C8 tertiary alcohol.

15. The method of claim 14, wherein the first organic solvent or the second organic solvent is t-butanol, 2-methyl-2-butanol, 2,3-dimethyl- 2-butanol, 2-methyl-2-pentanol, 3-methyl-3-pentanol, 3-ethyl-3-pentanol, 2,3-dimethyl-2-pentanol, 2,3-dimethyl-3-pentanol, 2,2,3-trimethyl-3-pentanol, 2-methyl-2-hexanol, or 3-methyl-3- hexanol.

16. The method of claim 15, wherein the first primary alcohol, the first secondary alcohol, the second primary alcohol, or the second secondary alcohol contains 1 to 18 carbon atoms.

17. The method of claim 16, wherein the oil source is plant oil, animal oil, waste grease, or a hydrolytic fraction thereof.

18. The method of claim 17, wherein the first lipase or the second lipase is immobilized on a carrier.

19. The method of claim 18, wherein the first lipase or the second lipase is candida antarctica lipase, thermomyces lanuginosa lipase, pseudomonas fluorescens lipase, pseudomonas cepacia lipase, or chromobacterium viscosum lipase.

20. The method of claim 19, wherein the first reacting step or the second reacting step is carried out at 0-95° C.

21. The method of claim 20, wherein the first reacting step or the second reacting step is carried out in 1-180 minutes.

22. The method of claim 21, further comprising heating the oil source to 150-215° C. and cooling the heated oil source down to the reaction temperature before the first mixing step.

23. The method of claim 22, further comprising adding an alkyl ester to the first solution before the first reacting step.

24. The method of claim 13, further comprising adding an alkyl ester to the first solution before the first reacting step.

25. The method of claim 13, wherein the first primary alcohol, the first secondary alcohol, the second primary alcohol, or the second secondary alcohol contains 1 to 18 carbon atoms.

26. The method of claim 13, wherein the oil source is plant oil, animal oil, waste grease, or a hydrolytic fraction thereof.

27. The method of claim 13, wherein the first lipase or the second lipase is immobilized on a carrier.

28. The method of claim 27, wherein the first lipase or the second lipase is candida antarctica lipase, thermomyces lanuginosa lipase, pseudomonas fluorescens lipase, pseudomonas cepacia lipase, or chromobacterium viscosum lipase.

29. The method of claim 13, wherein the first reacting step or the second reacting step is carried out at 0-95° C.

30. The method of claim 13, wherein the first reacting step or the second reacting step is carried out in 1-180 minutes.

31. The method of claim 13, further comprising heating the oil source to 150-215° C. and cooling the heated oil source down to the reaction temperature before the first mixing step.

32. The method of claim 13, wherein the first organic solvent or the second organic solvent is pyridine.

33. The method of claim 32, wherein the first primary alcohol, the first secondary alcohol, the second primary alcohol, or the second secondary alcohol contains 1 to 18 carbon atoms.

34. The method of claim 32, wherein the oil source is plant oil, animal oil, waste grease, or a hydrolytic fraction thereof.

35. The method of claim 32, wherein the first lipase or the second lipase is immobilized on a carrier.

36. The method of claim 35, wherein the first lipase or the second lipase is candida antarctica lipase, thermomyces lanuginosa lipase, pseudomonas fluorescens lipase, pseudomonas cepacia lipase, or chromobacterium viscosum lipase.

37. The method of claim 32, wherein the first reacting step or the second reacting step is carried out at 0-95° C.

38. The method of claim 32, wherein the first reacting step or the second reacting step is carried out in 1-180 minutes.

39. The method of claim 32, further comprising heating the oil source to 150-215 ° C. and cooling the heated oil source down to the reaction temperature before the first mixing step.

40. The method of claim 32, further comprising adding an alkyl ester to the first solution before the first reacting step.

* * * * *